United States Patent
Gärtner et al.

(10) Patent No.: US 9,199,924 B2
(45) Date of Patent: Dec. 1, 2015

(54) PROCESS FOR THE PREPARATION OF URETHANES

(75) Inventors: Felix Gärtner, Marburg (DE); Andreas Jacob, Marburg (DE); Jörg Sundermeyer, Marburg (DE); Stephan Klein, Shanghai (CN); Stefan Wershofen, Mönchengladbach (DE)

(73) Assignee: Bayer Intellectual Property GmbH, Monheim (DE)

( * ) Notice: Subject to any disclaimer, the term of this patent is extended or adjusted under 35 U.S.C. 154(b) by 51 days.

(21) Appl. No.: 13/816,526

(22) PCT Filed: Aug. 9, 2011

(86) PCT No.: PCT/EP2011/063718
§ 371 (c)(1),
(2), (4) Date: Aug. 5, 2013

(87) PCT Pub. No.: WO2012/020028
PCT Pub. Date: Feb. 16, 2012

(65) Prior Publication Data
US 2013/0303740 A1    Nov. 14, 2013

(30) Foreign Application Priority Data
Aug. 12, 2010 (DE) .......... 10 2010 039 250

(51) Int. Cl.
*B01J 31/22* (2006.01)
*C07C 263/00* (2006.01)
*C07C 269/04* (2006.01)
*C07C 245/08* (2006.01)
*C07C 251/24* (2006.01)
*C07D 215/26* (2006.01)
*C07D 213/30* (2006.01)

(52) U.S. Cl.
CPC ........... *C07C 263/00* (2013.01); *B01J 31/2243* (2013.01); *C07C 245/08* (2013.01); *C07C 251/24* (2013.01); *C07C 269/04* (2013.01); *C07D 213/30* (2013.01); *C07D 215/26* (2013.01); *B01J 2231/70* (2013.01); *B01J 2531/0241* (2013.01); *B01J 2531/16* (2013.01); *B01J 2531/821* (2013.01); *B01J 2531/822* (2013.01); *B01J 2531/827* (2013.01); *B01J 2531/828* (2013.01); *B01J 2531/845* (2013.01); *B01J 2531/847* (2013.01)

(58) Field of Classification Search
CPC ... C07C 263/00; C07C 269/04; B01J 31/2243
See application file for complete search history.

(56) References Cited

U.S. PATENT DOCUMENTS

| | | | |
|---|---|---|---|
| 3,481,967 A | 12/1969 | Ottmann et al. | |
| 4,266,070 A | 5/1981 | Moy | |
| 5,194,660 A | 3/1993 | Leung et al. | |
| 6,153,779 A | 11/2000 | Hess et al. | |
| 6,562,751 B2 | 5/2003 | Wang et al. | |
| 6,747,106 B2 | 6/2004 | Wang et al. | |
| 6,905,999 B2 | 6/2005 | Wang et al. | |
| 2009/0275771 A1 | 11/2009 | Jacob et al. | |
| 2010/0217029 A1 | 8/2010 | Sundermeyer et al. | |

FOREIGN PATENT DOCUMENTS

| | | |
|---|---|---|
| DE | 102008006881 A1 | 8/2009 |
| EP | 0967215 A2 | 12/1999 |
| WO | WO-01/68724 A2 | 9/2001 |
| WO | WO-03/018662 A1 | 3/2003 |
| WO | WO-2006131381 A1 | 12/2006 |
| WO | WO-2009/095164 A1 | 8/2009 |

OTHER PUBLICATIONS

Chatterjee, D., *Olefin epoxidation catalyzed by [RuIII(TDL)(tmeda)H2O ] complexes (TDL = Tridentate Schiff-base ligand; tmeda = tetramethylethylenediamine)* (2009), Journal of Molecular Catalysis A: Chemical, 310, S. 175, Fig. 1, S. 176, Fig. 2, pp. 174-179.

Priyarega, S., et al., *Synthetic and catalytic investigations of ruthenium (III) complexes with triphenylphospphine/triphenylarsine and tridentate Schiff base* (2007), Applied Organometallic Chemistry, 21, pp. 788-793.

Chatterjee, D., et al., *Oxidation of Organic Substrates Catalyzed by Novel Mixed-Ligand Chromium(III) Complexes* (2000), React. Catal. Len. vol. 71, No. 2, pp. 217-222.

Bhowon, M., et al., *Schiff base complexes of ruthenium (II) and their use as catalytic oxidants* (1999), Polyhedron 18, pp. 341-345.

Bagherzadeh, M., et al., *Efficient oxidation of olefins and sulfides catalyzed by manganese(III)-tridentate Schiff base complex using UHP as oxidant* (2008), Catalysis Communications 9, pp. 1600-1606.

Bagherzadeh, M., et al., *Synthesis, X-ray structure and study of a mixed ligand iron(III) complex with tridentate Schiff base as a homogenous catalyst in the efficient oxidation of sulfides* (2009), Inorganic Chemistry Communications 12, pp. 476-480.

(Continued)

*Primary Examiner* — Robert Havlin
(74) *Attorney, Agent, or Firm* — Drinker Biddle & Reath LLP

(57) ABSTRACT

The invention relates to a method for producing urethanes or ureas or mixtures of urethanes and ureas by oxidative carbonylation of organic amines in the presence of carbon monoxide, oxygen and a catalyst, where the catalyst used is a transition metal complex containing the structural feature: [Mn+(O~N~O)2−](n−2)+(L)m(Z−)n−2 and the method is carried out under halogen-free reaction conditions. The invention further relates to transition metal complexes containing said structural feature and also to the use of such transition metal complexes as catalysts in the production of urethanes or ureas or mixtures of urethanes and ureas.

9 Claims, No Drawings

(56) References Cited

OTHER PUBLICATIONS

Kurusu, Y., et al., *Die Autoxidation von Cumol in Gegenwart von Chelaten monomerer and polymerer Schiffscher Basen* (1975), Die Makromolekulare Chemie 176, pp. 3185-3200.

International Search Report for PCT/EP2011/063718 mailed Oct. 20, 2011.

Chatterjee et al., "Homogeneous Catalysis of C-H Bond Activation by a Novel Ruthenium(III)-Complex", React. Kinet. Catal. Lett. vol. 70, No. 1, pp. 147-151 (2000).

Chinese Office Action dated Jul. 3, 2014 for Chinese Patent Application No. 201180049440.0.

PROCESS FOR THE PREPARATION OF URETHANES

RELATED APPLICATIONS

This application is a national stage application (under 35 U.S.C. §371) of PCT/EP2011/063718, filed Aug. 9, 2011, which claims benefit of German application 10 2010 039 250.2, filed Aug. 12, 2010.

The invention relates to a process for the preparation of urethanes or ureas or mixtures of urethanes and ureas by the oxidative carbonylation of organic amines in the presence of carbon monoxide, oxygen and a catalyst, wherein the catalyst used is a transition metal complex containing the structural feature

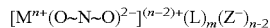
$[M^{n+}(O{\sim}N{\sim}O)^{2-}]^{(n-2)+}(L)_m(Z^-)_{n-2}$ and the process is carried out under halogen-free reaction conditions. The invention further relates to transition metal complexes containing the above structural feature and to the use of such transition metal complexes as catalysts in the preparation of urethanes or ureas or mixtures of urethanes and ureas.

One reaction step in the preparation of isocyanates, urethanes (also called carbamates) and ureas on the industrial scale is the reaction of the appropriate primary amine with phosgene. This produces large quantities of hydrogen chloride as a coupling product, which have to be disposed of or re-used in coupled processes at relatively high cost. Industry is therefore very interested in the development of non-coupled synthetic processes that manage without using phosgene and avoid hydrogen chloride as a coupling product.

Ottmann et al. (U.S. Pat. No. 3,481,967) describe a process for the preparation of aromatic isocyanates, wherein aromatic nitro compounds and carbon monoxide can be used in the presence of transition metal catalysts. These transition metal catalysts include cobalt iodide and titanium tetrachloride. However, industrially useful processes must be distinguished by a high conversion and a selectivity of more than 90%, wherever possible, in order to be successful. These requirements could only be met hitherto by reductive carbonylation processes, which start from aromatic nitro compounds and use expensive noble metal catalysts (B. K. Nefedov, V. I. Manov-Yuvenskii, S. S. Novikov, Doklady Chem. (Proc. Acad. Sci. USSR), 234, (1977), 347). It is usually difficult to recover the noble metal catalysts, so these processes are economically unacceptable.

WO 2006 131 381 A1 discloses the reductive carbonylation of aromatic nitro compounds in the presence of alcohols and acidic promoters to give urethanes. The need to use acidic promoters is a disadvantage. The reductive carbonylation of nitroaromatics with inexpensive cobalt complexes proceeds only very slowly in the absence of aniline and does not achieve a good turnover frequency (TOF). The reaction rate of the conversion of nitroaromatic to carbamate does not increase until aniline or an aminoaromatic has formed as an intermediate from the nitroaromatics, CO and protons. The disadvantage of said patent application is that the best results are achieved when the aniline and nitroaromatic components are present in a molar ratio of 2:1. However, it is not always easy to mix aromatic amines and aromatic nitro compounds. Thus, for example, it is sufficiently well-known that the thermal stability of dinitrotoluene decreases in the presence of amines, which can entail safety risks.

Industrial and scientific research has therefore concentrated overwhelmingly on the development of processes wherein aromatic amino compounds in the presence of carbon monoxide and an organic compound containing hydroxyl groups are converted by oxidative carbonylation in the presence of oxygen to N-arylurethanes, which can be converted to the corresponding N-arylisocyanates in a subsequent process step.

This is exemplified in U.S. Pat. No. 4,266,070, wherein aromatic amines are reacted in the presence of $Co_2(CO)_8$ as catalyst, an organic compound containing hydroxyl groups, and an unsaturated organic component. The last of these is necessary for ensuring high selectivities. It is also expressly pointed out that no oxidizing agent, e.g. oxygen, is used.

Benedini et al. were the first to use [$Co^{II}$(salen)] (salen=N, N'-disalicylidene-ethylenediamine) as a catalyst for transforming aromatic or aliphatic primary amines to the corresponding urethanes or ureas in the presence of methanol (F. Benedini, M. Nali, B. Rindone, S. Tollari, J. Mol. Catal., 1986, 34, 155-161; G. Maddinelli, M. Nali, B. Rindone, S. Tollari, J. Mol. Catal., 1987, 39, 71-77). Disadvantages of this process are especially the long reaction times of up to 48 hours and also the immensely high catalyst concentrations (up to 20 mol %). The selectivities are moderate to good and generally yield a product mixture of the corresponding urethanes and ureas.

U.S. Pat. No. 5,194,660, which describes the oxidative carbonylation of aromatic amines in the presence of carbon monoxide and an organic compound containing hydroxyl groups, as well as oxygen as oxidizing agent, discloses the use of transition metal complex catalysts consisting of a central metal and macrocyclic ligands. The latter are preferably tetradentate ligands from the group comprising porphyrins, phthalocyanines and Schiff bases. Among the ligands from the group comprising Schiff bases, those with six (or even more) coordination sites are also disclosed (column 7, lines 9-11). Disadvantages of this process include the use of large quantities of alkali metal halide, usually sodium iodide, as promoter. The alkali metal is used in excess relative to the actual catalyst (cf. Examples). Barely controllable corrosion problems due to the large quantities of halogen are another weakness of this process.

The object was therefore to provide a process for the preparation of urethanes and/or ureas by the oxidative carbonylation of the appropriate primary amines in the presence of oxygen, said process being distinguished by high conversions and selectivities without the use of halogen-containing promoters.

The object was achieved by a process for the preparation of urethanes or ureas or mixtures of urethanes and ureas by the oxidative carbonylation of organic amines containing primary amino groups in the presence of carbon monoxide, oxygen and a catalyst, wherein the catalyst used is a transition metal complex, preferably a mononuclear transition metal complex, containing the structural feature $[M^{n+}(O{\sim}N{\sim}O)^{2-}]^{(n-2)+}(L)_m(Z^-)_{n-2}$, M being a transition metal selected from groups 5, 6 and 8 to 11 of the periodic table of the elements, n being 2 or 3, $(O{\sim}N{\sim}O)^{2-}$ being a tridentate, dianionic, preferably halogen-free chelating ligand coordinating with M via two oxygen atoms and one nitrogen atom, L being a neutral ligand, m being 0, 1, 2 or 3 and $Z^-$ being a monoanionic ligand other than halide (cf. below for details);

and the process is carried out under halogen-free reaction conditions, which are also illustrated in detail below.

Suitable transition metals M from groups 5, 6 and 8 to 11 of the periodic table of the elements in the transition metal complexes containing the structural feature $[M^{n+}(O\sim N\sim O)^{2-}]^{(n-2)+}(L)_m(Z^-)_{n-2}$, which are to be used in the process according to the invention for the oxidative carbonylation of organic amines are especially vanadium, chromium, iron, cobalt, nickel, copper, zirconium, niobium, molybdenum, ruthenium, rhodium, palladium, silver, hafnium, tantalum, tungsten, osmium, iridium, platinum and gold; preferred metals are cobalt, chromium, nickel, copper, some "4d metals", such as rhodium and ruthenium, and "5d metals", such as iridium and platinum. Cobalt, nickel, copper, rhodium, ruthenium, iridium and platinum are particularly preferred. The invention thus relates in particular to a process for the preparation of urethanes or ureas or mixtures of urethanes and ureas by the oxidative carbonylation of organic amines wherein the transition metal catalyst used contains a transition metal M selected from the group comprising Co, Cr, Ni, Cu, Rh, Ru, Ir and Pt, and particularly preferably to a process for the preparation of urethanes or ureas or mixtures of urethanes and ureas by the oxidative carbonylation of organic amines wherein the transition metal catalyst used contains a transition metal M selected from the group comprising Co, Ni, Cu, Rh, Ru, Ir and Pt. In one very particularly preferred embodiment of the process according to the invention for the oxidative carbonylation of organic amines, the transition metal M is cobalt. The nomenclature "4d metal" within the framework of the present invention denotes a transition metal with an electronic configuration of $4d^0$ to $4d^{10}$. "3d and 5d metals" are correspondingly defined.

The nomenclature of the groups of the periodic table in the present patent application is in accordance with the IUPAC recommendation of 1988 (cf. G. J. Leigh, Nomenclature of Inorganic Chemistry, Blackwell Scientific Publications, London, 1990, p. 282). For the terms "number of coordination sites per ligand", "chelating ligand" and "number of rings per molecule" of complexes, cf. Hollemann, Wiberg, Lehrbuch der Anorganischen Chemie, 101$^{st}$ edition, Walter de Gruyter & Co. Berlin, 1995, pp 1206, 1208 to 1211.

The invention further relates in particular to a process wherein the neutral ligand L is selected from the group comprising:
water, azaaromatics, cyclic or acyclic amines, cyclic or acyclic carboxamides, cyclic or acyclic carboxylic acid esters, cyclic or acyclic ketones, cyclic or acyclic ketimines, aliphatic ethers, aliphatic or aromatic alcohols, sulfoxides, cyclic or acyclic organocarbonates and nitriles, preference being afforded to halogen-free representatives of said classes of compounds.

The invention further relates to a process wherein the monoanionic ligand $Z^-$ is selected from the group comprising:
sulfonates, preferably triflate, tosylate and mesylate, particularly preferably tosylate and mesylate;
carboxylates, preferably acetate, trifluoroacetate and benzoate, particularly preferably acetate and benzoate;
pseudohalides, preferably cyanide, cyanate, thiocyanate and azide; perfluorinated non-metal coordination compounds, preferably $[BF_4]^-$, $[PF_6]^-$ and $[SbF_6]^-$;
anions of inorganic acids, preferably nitrate, hydrogensulfate and fluorosulfate, particularly preferably nitrate and hydrogensulfate; and
methylsulfate,
tosylate, mesylate, acetate, benzoate, cyanide, cyanate, thiocyanate, azide, nitrate, hydrogensulfate and methylsulfate being very particularly preferred.

Examples of preferred azaaromatics as neutral ligands L are pyridine, quinoline, 1,2-diazine (pyridazine), 1,3-diazine (pyrimidine), 1,4-diazine (pyrazine), 1,3,5-triazine, imidazole, N-methylimidazole, oxazole, thiazole, triazole and N-methyltriazole.

Examples of preferred cyclic or acyclic amines as neutral ligands L are n-butylamine, ethylamine, diethylamine, triethylamine, aniline, N-methylaniline, N,N-dimethylaniline, pyrrolidine, N-methylpyrrolidine, piperidine, N-methylpiperidine, morpholine and N-methylmorpholine. In the case of primary amines as ligands L, L is preferably identical to the starting amine used as educt, so as to avoid unwanted reactions. Such primary amines are particularly preferably aniline and toluoylene-diamine.

Examples of preferred cyclic or acyclic carboxamides as neutral ligands L are N,N-dimethylformamide, N,N-dimethylacetamide, N,N-dimethylbenzamide, 1-methyl-2-pyrrolidone, 1-methyl-2-piperidone, ε-caprolactam and 1-methylcaprolactam.

Examples of preferred cyclic or acyclic carboxylic acid esters as neutral ligands L are ε-caprolactone, ethyl acetate, methyl butylate and cyclohexyl acetate.

Examples of preferred cyclic or acyclic ketimines as neutral ligands L are compounds of the general formula $R^I R^{II} C=NR^{III}$, where $R^I$, $R^{II}$ and $R^{III}$ independently of one another are cyclic or acyclic alkyl groups, aryl or heteroaryl groups or a bridging alkylene group. Particularly preferably, the radicals $R^I$, $R^{II}$ and $R^{III}$ do not contain halogens.

Examples of preferred aliphatic ethers as neutral ligands L are diethyl ether, dibutyl ether, tetrahydrofuran, 1,2-dimethoxyethane and 1,4-dioxane.

Examples of preferred aliphatic or aromatic alcohols as neutral ligands L are methanol, ethanol, n-butanol, 2,2,2-trifluoroethanol and phenol. Methanol, ethanol, n-butanol and phenol are particularly preferred.

One example of preferred sulfoxides as neutral ligands L is dimethyl sulfoxide.

Examples of preferred cyclic or acyclic organocarbonates as neutral ligands L are dimethyl carbonate, diethyl carbonate and propylene carbonate.

Examples of preferred nitriles as neutral ligands L are acetonitrile and propionitrile.

The ligands L can also be absent in the catalyst stage isolated as a substance. In solution the ligands L can be solvent molecules that can easily be substituted by the starting amines to be reacted.

Examples of preferred carboxylates as monoanionic ligands $Z^-$ are benzoate, acetate, trifluoroacetate and formate. Benzoate, acetate and formate are particularly preferred.

Examples of preferred sulfonates as monoanionic ligands $Z^-$ are triflate ($CF_3SO_3^-$) and tosylate ($CH_3-C_6H_4-SO_3^-$, all isomers). Tosylate is particularly preferred.

Examples of preferred pseudohalides as monoanionic ligands $Z^-$ are $CN^-$, $SCN^-$, $OCN^-$ and $N_3^-$.

Examples of preferred perfluorinated non-metal coordination compounds as monoanionic ligands $Z^-$ are $[BF_4]^-$, $[PF_6]^-$ and $[SbF_6]^-$.

The invention further relates in particular to a process wherein the dianionic chelating ligand $(O\sim N\sim O)^{2-}$ is derived by deprotonation of all the OH groups (that are not part of the substituents $R^1$ or $R^2$) of neutral chelating ligands selected from the group comprising:

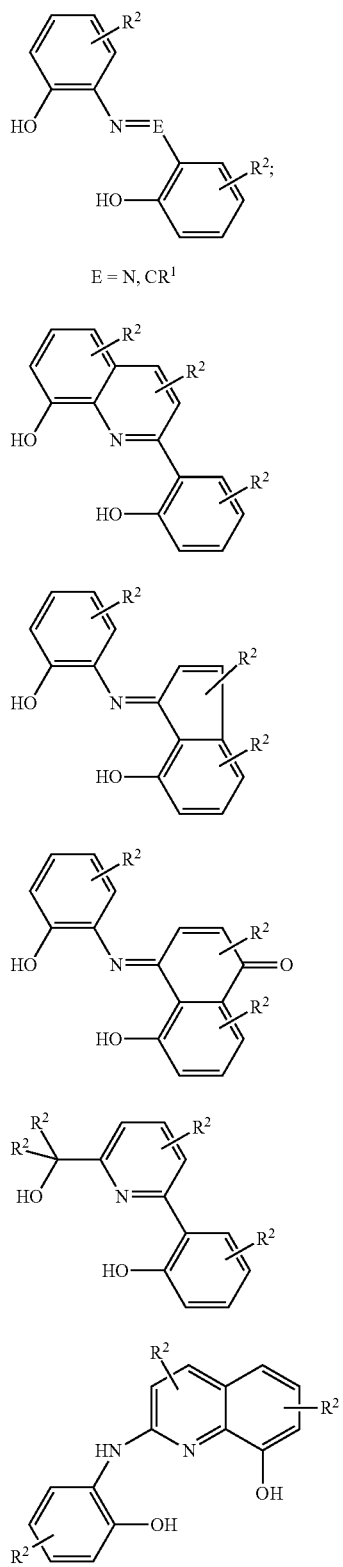
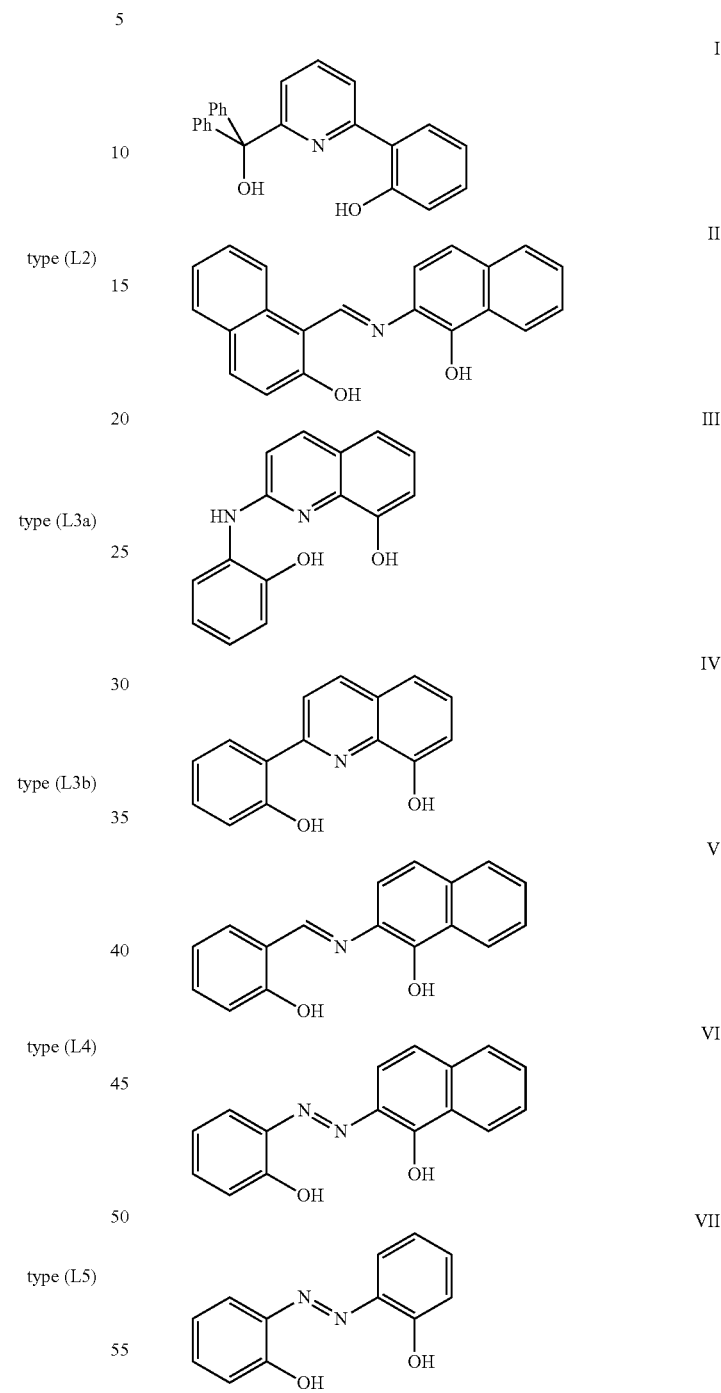

(cf. detailed explanations below for the precise definitions of $R^1$ and $R^2$).

Particularly preferred embodiments of the process according to the invention are those wherein the dianionic chelating ligand $(O\sim N\sim O)^{2-}$ is derived by deprotonation of all the OH groups of neutral chelating ligands selected from the group comprising:

Chelating ligands V and VII, especially VII, are very particularly preferred.

The invention further relates in particular to transition metal complexes, preferably mononuclear transition metal complexes, containing the structural feature $[M^{n+}(O\sim N\sim O)^{2-}]^{(n-2)+}(L)_m(Z^-)_{n-2}$, wherein M is a transition metal selected from groups 5, 6 and 8 to 11 of the periodic table of the elements;

n is 2 or 3;

$(O\sim N\sim O)^{2-}$ is a tridentate, dianionic, halogen-free chelating ligand coordinating with M via two oxygen atoms and one nitrogen atom, which is derived by deprotonation of all the OH groups of neutral chelating ligands selected from the group comprising:

type (L1)

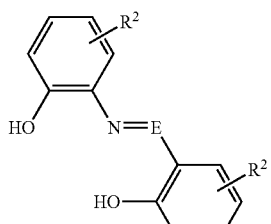

E = N, CR¹ type (L2)

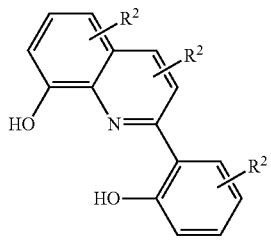

type (L3a)

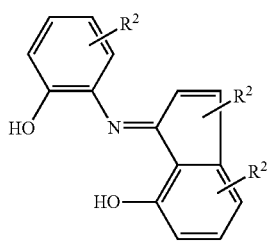

type (L3b)

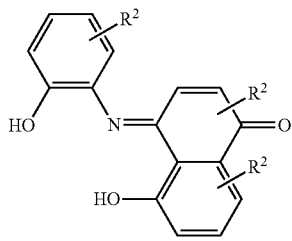

type (L4)

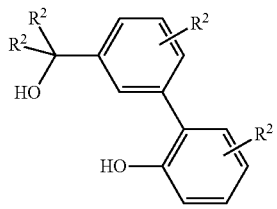

type (L5)

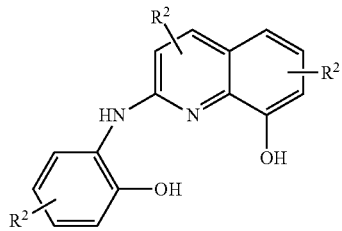

L is a neutral ligand selected from the group comprising:
  water, azaaromatics, cyclic or acyclic amines, cyclic or acyclic carboxamides, cyclic or acyclic carboxylic acid esters, cyclic or acyclic ketones, cyclic or acyclic ketimines, aliphatic ethers, aliphatic or aromatic alcohols, sulfoxides, formamides, cyclic or acyclic organocarbonates and nitriles, preference being afforded to the halogen-free representatives of said classes of compounds;

m is 0, 1, 2 or 3; and $Z^-$ is a monoanionic ligand selected from the group comprising:
  sulfonates, preferably triflate, tosylate and mesylate, particularly preferably tosylate and mesylate;
  carboxylates, preferably acetate, trifluoroacetate and benzoate, particularly preferably acetate and benzoate;
  pseudohalides, preferably cyanide, cyanate, thiocyanate and azide;
  perfluorinated non-metal coordination compounds, preferably $[BF_4]^-$, $[PF_6]^-$ and $[SbF_6]^-$;
  anions of inorganic acids, preferably nitrate, hydrogensulfate and fluorosulfate, particularly preferably nitrate and hydrogensulfate; and
  methylsulfate,
  tosylate, mesylate, acetate, benzoate, cyanide, cyanate, thiocyanate, azide, nitrate, hydrogensulfate and methylsulfate being very particularly preferred.

The invention further relates to the use of such transition metal complexes as catalysts in processes for the preparation of urethanes or ureas or mixtures of urethanes and ureas.

In preferred transition metal complexes, $(O\sim N\sim O)^{2-}$ is a tridentate, dianionic chelating ligand coordinating with M via two oxygen atoms and one nitrogen atom, which is derived by deprotonation of all the OH groups of neutral chelating ligands selected from the group comprising:

I

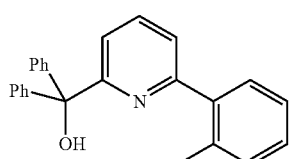

II

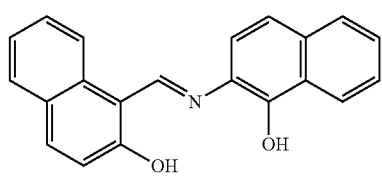

Furthermore, in preferred transition metal complexes, the transition metal M is selected from the group comprising Co, Cr, Ni, Cu, Rh, Ru, Ir and Pt, particularly preferably Co, Ni, Cu, Rh, Ru, Ir and Pt, Co being very particularly preferred.

Very particularly preferred, specific representatives of the individual constituents of the transition metal complexes according to the invention (transition metals M, neutral ligands L and monoanionic ligands $Z^-$) are the same as those already defined above. The invention therefore relates very particularly preferably to transition metal complexes as defined above in which
- the transition metal M is cobalt;
- the dianionic chelating ligands $(O{\sim}N{\sim}O)^{2-}$ are derived by deprotonation of all the OH groups of neutral chelating ligands selected from the group comprising:
    V and VII; and
- the monoanionic ligands $Z^-$ are selected from the group comprising:
    tosylate, mesylate, acetate, benzoate, cyanide, cyanate, thiocyanate, azide, nitrate, hydrogensulfate and methylsulfate.

The process according to the invention is carried out under halogen-free reaction conditions. In other words, under the reaction conditions, halogens ("Hal")
(1) in elemental form ($Hal_2$—including interhalogen compounds—or Hal.) or
(2) in ionic form ($Hal^-$ or polyhalides $Hal_n^-$, e.g. $I_3^-$) or
(3) in the form of their oxo acids, including their salts
are neither added nor released in the course of the reaction.

This encompasses on the one hand the fact that there is absolutely no addition of halogen-containing promoters in the sense of U.S. Pat. No. 5,194,660. This is how the process according to the invention differs from said US patent specification, where 0.05 wt % to 10 wt %, preferably 0.1 wt % to 5 wt % (based on the initial quantity of all the components), of a halogen-containing promoter is used (column 9, lines 49-53). Within the framework of the present invention "halogen-containing promoters" are understood as meaning:
- ionic metal halides, such as those of alkali metals (e.g. sodium chloride, potassium chloride, sodium bromide, sodium iodide) or of alkaline earth metals (e.g. calcium chloride, strontium bromide, barium iodide);
- so-called "onium ions" of the general formula $[(R^{IV})_t(R^V)_t(R^{VI})_t(R^{VII})_u Y]^+ Hal^-$, where $R^{IV}$ to $R^{VII}$ independently of one another are hydrogen and aliphatic or aromatic radicals carrying any substituents, Y is the elements nitrogen, phosphorus, arsenic, antimony, sulfur, selenium and tellurium, and Hal is the halides fluorine, chlorine, bromine and iodine, and u can be 0 or 1;
- oxo acids of halogens and their salts (e.g. perchloric acid and its salts);
- complex compounds containing halide ions ($Hal^-$);
- organic halogen compounds ("Org-Hal"), in which the carbon-halogen bond can easily be cleaved homolytically (Org-Hal→Org.+Hal.) or hetero-lytically (Org-Hal→$Org^+$+$Hal^-$–organic "halides") as a result of resonance stabilization of the resulting radicals (Org.) or carbocations ($Org^+$), e.g. as in $Ph_3CCl$, and
- halogen molecules.

One advantage of working without halogen-containing promoters—apart from saving the cost of preparing the necessary reagents—is that said halogen-containing promoters do not have to be separated off, recovered and/or recycled. It is also ecologically desirable not to use halogen-containing promoters.

Halogens neither being added nor released in the process according to the invention encompasses on the other hand the fact that halogen compounds in which the parent molecule is joined to the halogen via a strong bond that is stable under the reaction conditions conventionally used according to the invention (cf. below for details), so that no halogens, halides or hydrogen halide are released, are not understood as halogen-containing promoters. The use of such compounds does not therefore constitute a deviation from the "halogen-free reaction conditions" in the sense of the present invention. Such stable halogen-containing compounds that are not to be classed as promoters are especially
- halogen-containing ions used as monoanions $Z^-$, such as perfluorinated non-metal coordination compounds ($[BF_4]^-$, $[PF_6]^-$, $[SbF_6]^-$), triflate, trifluoroacetate and fluorosulfate;
- halogen-containing solvents (such as dichloromethane, chloroform, chlorobenzene, bromobenzene, etc.); and
- alcohols substituted by halogens on the carbon skeleton (such as trifluoroethanol).

In industrial practice, however, it is conceivable for a certain content of halogen-containing compounds corresponding in principle to the above definition of halogen-containing promoters to be unavoidably present in the carbonylation reaction, e.g. as a result of impurities in any solvent that may be used or in the educts, or impurities originating from the preparation of the catalyst and/or ligand(s). Such traces of halogen-containing compounds that are formally considered halogen-containing promoters are not necessary for the functioning of the process according to the invention, but generally do not interfere either. Therefore, in industrial practice, it is generally excessive and uneconomic to want to use expensive purification processes to completely remove such traces of halogen-containing compounds originating from impurities. However, in the process according to the invention, such a content of halogen-containing compounds which originate from impurities and have not been added deliberately, and which are formally considered halogen-containing promoters, is always less than 0.04 wt %, preferably less than 0.03 wt %, particularly preferably less than 0.02 wt % and very particularly preferably less than 0.001 wt %, based on the total weight of the reaction mixture. If educts and solvents free of halogen-containing promoters are available at an economically justifiable price, their use is extremely particularly preferred.

It was found that transition metal complexes containing the smallest common structural unit of the $(O{\sim}N{\sim}O)^{2-}$ chelating ligands, shown in scheme (i), are preferably suitable for the oxidative carbonylation of organic amines without the addition of halogen-containing promoters.

Scheme (i)

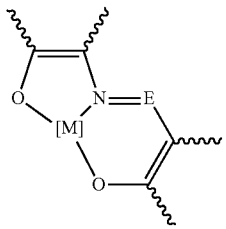

Here and below, E is N or C—$R^1$.

Within the framework of the present invention, $R^1$ is hydrogen, an alkyl radical having 1 to 20 carbon atoms, an aryl or heteroaryl group, a group OR, in which R is hydrogen or an alkyl group having 1 to 20 carbon atoms, or a group NRR', in which R and R' independently of one another are hydrogen or an aryl or alkyl group having 1 to 20 C atoms, or together can form a ring system with the nitrogen atom as a heteroatom. Preferably, $R^1$ is an alkyl radical having 1 to 20 carbon atoms, an aryl or heteroaryl group, a group OR, in which R is hydrogen or an alkyl group having 1 to 20 carbon atoms, or a group NRR', in which R and R' independently of one another are hydrogen or an aryl or alkyl group having 1 to 20 C atoms, or together can form a ring system with the nitrogen atom as a heteroatom. Here and below, all the radicals R, R' and $R^i$ (i=Arabic numeral) are preferably halogen-free.

It generally applies hereafter that, when they occur several times, all the radicals R, R' and $R^i$ (i=Arabic numeral) of a given structure can be identical but do not have to be; rather, they can be selected independently of one another from the appropriate sets of definitions for the radicals R, R' and $R^i$ (i=Arabic numeral).

"~~~" represents organic radicals as specified in greater detail below. Here and below, these radicals are again preferably halogen-free.

The notation [M], here and below, stands for a di- or trivalent transition metal $M^{n+}$, as defined above, and includes the fact that the coordination sphere around the metal is filled not only with the dianionic chelating ligand but also with other neutral ligands L or monoanionic ligands $Z^-$ up to a coordination number of 4, 5, 6 or 7, corresponding to the general structural feature $[M^{n+}(O{\sim}N{\sim}O)^{2-}]^{(n-2)+}(L)_m(Z^-)_{n-2}$ defined above. Thus: $[M]=M^{2+}(L)_1$ (=coordination number 4), or $[M]=M^{2+}(L)_2$ (=coordination number 5), or $[M]=M^{2+}(L)_3$ (=coordination number 6), or $[M]=M^{2+}(L)_4$ (=coordination number 7), or $[M]=M^{3+}(Z^-)_1$ (=coordination number 4), or $[M]=M^{3+}(L)_1(Z^-)_1$ (=coordination number 5), or $[M]=M^{3+}(L)_2(Z^-)_1$ (=coordination number 6), or $[M]=M^{3+}(L)_3(Z^-)_1$ (=coordination number 7). In this nomenclature the indices 1 to 3 associated with the neutral ligands (L), refer to the coordination sites belonging to these ligands, i.e. one tridentate ligand ("1×L~L~L", e.g. terpyridine) is denoted by $(L)_3$ in exactly the same way as three monodentate ligands ("3×L", e.g. pyridine).

Here and in all the schemes below, [M] preferably stands for $M^{n+}(L)_m(Z^-)_{n-2}$, in which M is a transition metal selected from Co, Cr, Ni, Cu and some "4d metals", such as Rh and Ru, and "5d metals", such as Ir and Pt, and m and n are as defined above. Particularly preferably, M is selected from the group comprising Co, Ni, Cu, Rh, Ru, Ir and Pt. Very particularly preferably, M is cobalt. The reason why cobalt is the preferred central metal lies in its low price and the high activity of the cobalt complexes.

In the sense of the present invention, the term "alkyl" includes acyclic and cyclic saturated hydrocarbon radicals which can be branched or linear and unsubstituted or at least monosubstituted. As examples of suitable alkyl radicals which can be unsubstituted or mono- or polysubstituted, there may be mentioned methyl, ethyl, n-propyl, isopropyl, n-butyl, isobutyl, 2-butyl, tert-butyl, n-pentyl, 2-pentyl, 3-pentyl, isopentyl, neopentyl, n-hexyl, 2-hexyl, 3-hexyl, n-heptyl, n-octyl, —C(H)($C_2H_5$)$_2$, —C(H)(n-$C_3H_7$)$_2$ and —$CH_2$—$CH_2$—C(H)($CH_3$)—($CH_2$)$_3$—$CH_3$.

In the sense of the present invention, the term "aryl" denotes a mono- or polycyclic, preferably mono- or bicyclic, aromatic hydrocarbon radical preferably having 6, 10 or 14 carbon atoms. An aryl radical can be unsubstituted, monosubstituted or polysubstituted by identical or different substituents. As examples of suitable aryl radicals, there may be mentioned phenyl, 1-naphthyl, 2-naphthyl and anthracenyl. A phenyl radical is particularly preferred.

In the sense of the present invention, the term "heteroaryl" denotes a mono- or polycyclic, preferably mono-, bi- or tricyclic, aromatic hydrocarbon radical having preferably 5, 6, 7, 8, 9, 10, 11, 12, 13 or 14 carbon atoms, particularly preferably 5, 6, 9, 10, 13 or 14 carbon atoms and very particularly preferably 5 or 6 carbon atoms, in which one or more carbon atoms have each been replaced by a heteroatom selected independently of one another from the group comprising oxygen, sulfur and nitrogen (NH). Heteroaryl radicals can contain preferably 1, 2, 3, 4 or 5 heteroatoms, particularly preferably 1, 2 or 3 heteroatoms, selected independently of one another from the group comprising oxygen, sulfur and nitrogen (NH), as ring members. A heteroaryl radical can be unsubstituted, monosubstituted or polysubstituted by identical or different substituents. As examples of suitable heteroaryl radicals, there may be mentioned indolizinyl, benzimidazolyl, tetrazolyl, triazinyl, isoxazolyl, phthalazinyl, carbazolyl, carbolinyl, diazanaphthyl, thienyl, furyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, pyrimidinyl, indazolyl, quinoxalinyl, quinazolinyl, quinolinyl, naphthridinyl and isoquinolinyl.

In the sense of the present invention, aryl or heteroaryl radicals can be fused with a mono- or bicyclic ring system. Examples which may be mentioned of aryl radicals fused with a mono- or bicyclic ring system are (2,3)-dihydrobenzo[b]thiophenyl, (2,3)-dihydro-1H-indenyl, indolinyl, (2,3)-dihydrobenzofuranyl, (2,3)-dihydrobenzo-[d]oxazolyl, benzo[d][1,3]dioxolyl, benzo[d][1,3]oxathiolyl, isoindolinyl, (1,3)-dihydroisobenzofuranyl, (1,3)-dihydrobenzo[c]thiophenyl, (1,2,3,4)-tetrahydro-naphthyl, (1,2,3,4)-tetrahydroquinolinyl, chromanyl, thiochromanyl, (1,2,3,4)-tetra-hydroisoquinolinyl, (1,2,3,4)-tetrahydroquinoxalinyl, (3,4)-dihydro-2H-benzo[b]-[1,4]oxazinyl, (3,4)-dihydro-2H-benzo[b][1,4]thiazinyl, (2,3)-dihydrobenzo[b][1,4]-dioxinyl, (2,3)-dihydrobenzo[b][1,4]oxathiinyl, (6,7,8,9)-tetrahydro-5H-benzo[7]-annulenyl, (2,3,4,5)-tetrahydro-1H-benzo[b]azepinyl and (2,3,4,5)-tetrahydro-1H-benzo[c]azepinyl.

If one of the aforementioned radicals is mono- or polysubstituted, possible substituents are all the ones familiar to those skilled in the art, which are preferably selected independently of one another from the group comprising F, Cl, Br, I, —NO$_2$, —CN, —OH, —SH, —NH$_2$, —N(C$_{1-5}$-alkyl)$_2$, —N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —NH—C(=O)—O—C$_{1-5}$-alkyl, —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$-alkyl)$_2$, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H. Particularly preferred substituents can be selected independently of one another from the group comprising —NO$_2$, —CN, —OH, —SH, —NH$_2$, —N(C$_{1-5}$-alkyl)$_2$, —N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —NH—C(=O)—O—C$_{1-5}$-alkyl, —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$-alkyl)$_2$, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H. Very particularly preferably, the substituents are halogen-free.

A common structural element of the chelating ligands shown in scheme (i) is the presence of an aromatic, heteroaromatic or vinylic structural group [—O—C=C—N=] in which one of the two ligand-binding O atoms is separated from the ligand-binding N atom by two sp$^2$-hybridized carbon atoms. Thus, an example of a typical structural unit of such chelating ligands is the ligand structural group 1-amino-2-hydroxyphenylene. As N,O ligands with this backbone themselves have redox activity, they are described as "redox non-innocent" (for the term "redox non-innocence", cf. K. Wieghardt et al., Dalton Transactions, 2003, 1126-1132). The chelating ligands shown generally in scheme (i) and described in greater detail below meet the criterion of ligand redox non-innocence.

It was found in particular that transition metal complexes which correspond to the special embodiments of types (1) to (5) shown in scheme (ii) (corresponding to ligand types (L1) to (L5)) are particularly preferably suitable for the oxidative carbonylation of organic amines without the addition of halogen-containing promoters.

Scheme (ii)

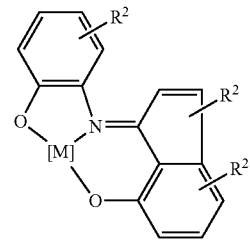

type (1)

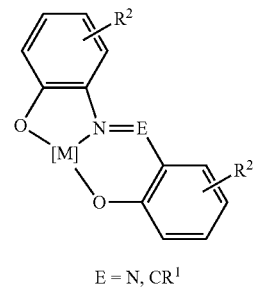

E = N, CR$^1$ type (2)

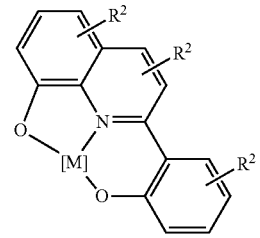

type (3)

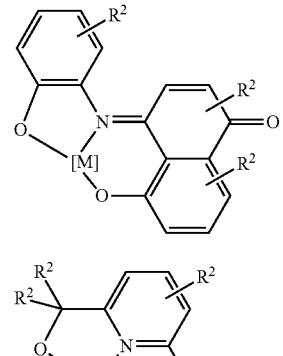

type (4)

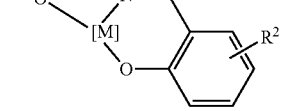

type (5)

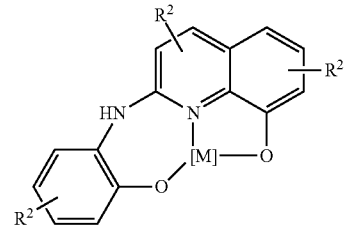

Within the framework of the present invention, R$^2$ is hydrogen, an alkyl group having 1 to 20 carbon atoms, an aryl group or heteroaryl group, the aryl group or heteroaryl group each being either joined via a bond to the tridentate ligand (which preferably contains a salicylate structural member) or fused to the latter via two C—C bonds, a keto group —COR or else —COOR, —COOH, OH, OR or NRR', R and R' being as defined above and it being possible for $R^2$ to substitute the aromatic ring 1 to 4 times.

Within the framework of the present invention, $R^3$ and $R^4$ independently of one another are hydrogen, an alkyl group having 1 to 20 carbon atoms, an aryl or heteroaryl group, a keto group —COR or else —COOR, —COOH, OH, OR or NRR', R and R' being as defined above.

It was also found that transition metal complexes having one of the structures shown in scheme (iii) are likewise particularly preferably suitable for the oxidative carbonylation of organic amines without the addition of halogen-containing promoters.

Scheme (iii)

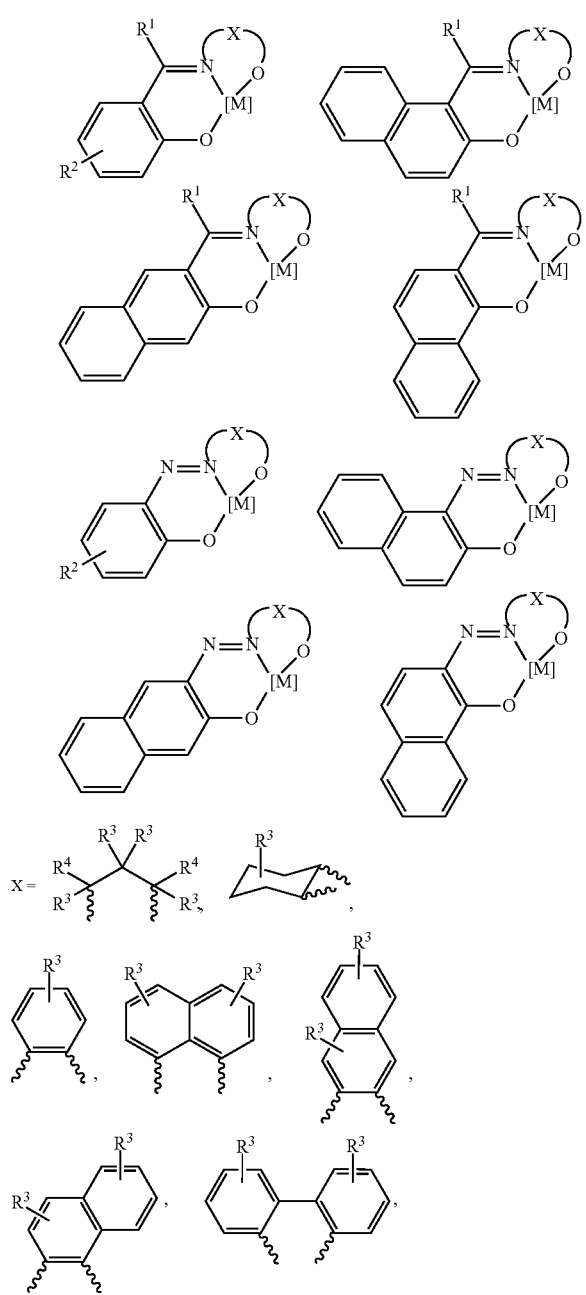

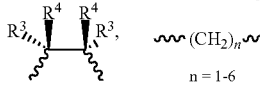

Here and below, X is any alkylene or arylene structural unit. This unit X can also be joined via its central substituents $R^3$ or $R^4$ to other molecular, macromolecular or inorganic structural elements.

Particularly preferably, [M] is [Co]. In this connection cf. also R. K. Parashar, R. C. Sharma, A. Kumar, G. Mohan, Inorg. Chim. Acta 1988, 151, 201-208; T. Abe, Bull. Chem. Soc. Jpn 1958, 31, 904-907.

Very particularly preferred transition metal complexes of schemes (i) to (iii) with chelating ligands $(O{\sim}N{\sim}O)^{2-}$ include those in which the chelating ligands occupy three meridional coordination sites around the central metal, the three remaining meridional coordination sites being occupied either by the O ligand functionality of a neighbouring M(O~N~O) complex in the dinuclear molecular association, additionally bridging via free O electron pairs, or by solvent molecules or substrate molecules with donor functionality, or any other ligands. A meridional (shortened to mer-) ligand arrangement is understood as meaning that the three coordinating ligand-binding atoms and the central metal atom lie approximately in a plane (in this connection cf. also Joan Ribas Gispert, Coordination Chemistry, Wiley-VCH Weinheim 2008, Chapter 4.3.2 Geometrical Isomers, page 102). Extremely particularly preferred transition metal complexes of schemes (i) to (iii) are those in which [M] is [Co] and in which the chelating ligands occupy three meridional coordination sites around the cobalt.

Very particularly preferred compounds of scheme (iii) are the highly active transition metal complexes of the Sap type (Sap=salicylidene-aminophenol, formula A), R' being particularly preferably H, methyl (Me) or phenyl (Ph) and very particularly preferably methyl (Me) or phenyl (Ph).

formula A

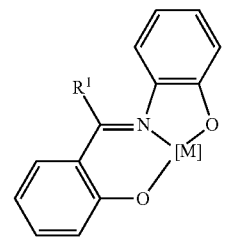

Other very particularly preferred compounds of scheme (iii) are those of the Abp type (Abp=azobisphenol, formula B).

formula B

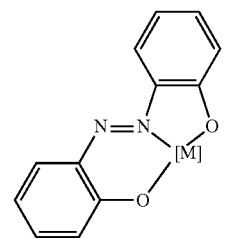

Complexes of the cobalt-Sap and cobalt-Abp types ([M]= [Co] in formulae A and B) have proved very particularly suitable as catalysts. Their common structural element consists of salicylaldehyde and aminophenol structural groups joined by an additional atom (carbon, nitrogen).

Other catalysts which can be used in the process according to the invention are transition metal complex compounds with other dianionic $N_1O_2$ chelating ligands that combine carboxylate, azaaromatic, phenate and/or metallated carboxamide groups. Suitable ligands with particularly preferred structural elements are described in greater detail in schemes (iv) and (v) below:

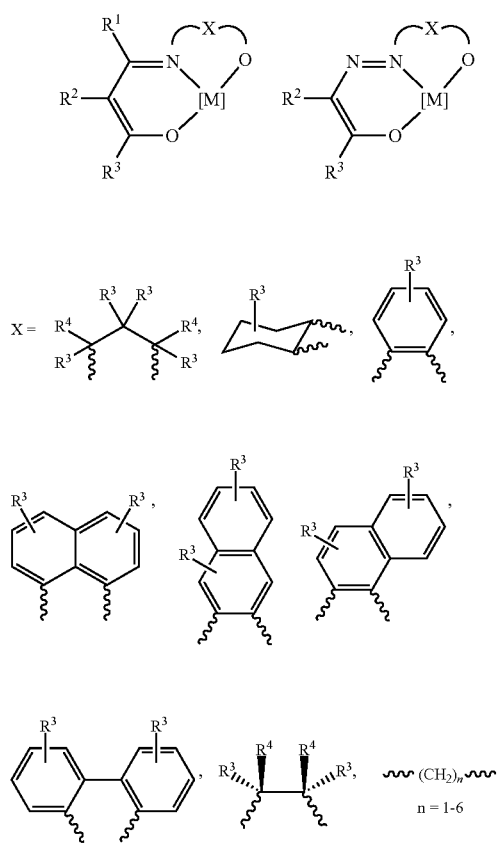

In scheme (iv) $R^1$, $R^2$, $R^3$, $R^4$, X and [M] are defined in exactly the same way as above.

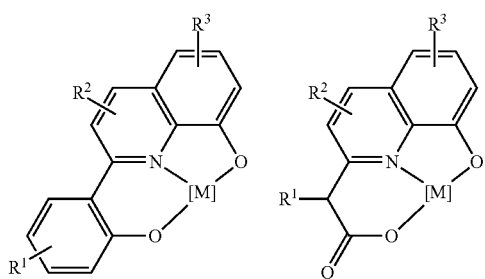

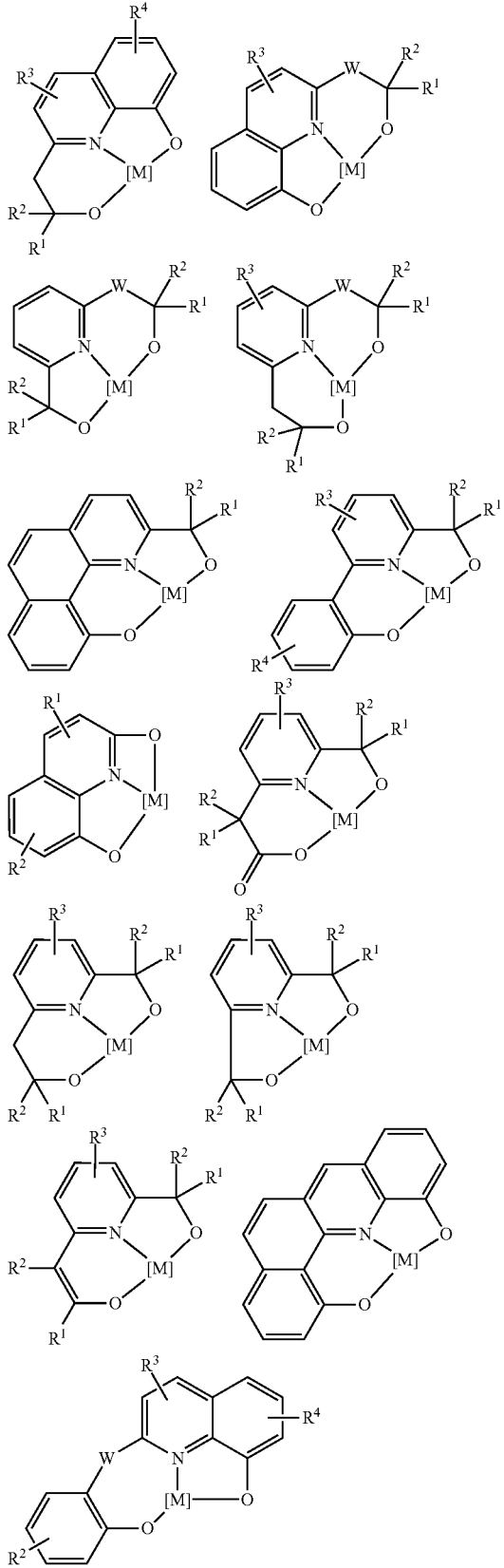

In scheme (v) W is NH, N-alkyl, N-aryl, O, S, CO, $CH_2$, CHR (where R=$C_1$-$C_{20}$-alkyl), $CR_2$ or aryl.

In schemes (iv) and (v) [M] is again preferably [Co]. Here, as in schemes (i) to (iii), the chelating ligands also preferably occupy three meridional coordination sites around the cobalt, the three remaining meridional coordination sites being occupied either by the O ligand functionality of a neighbouring M(O~N~O) complex in the dinuclear molecular association, additionally bridging via free O electron pairs, or by solvent molecules or substrate molecules with donor functionality, or any other ligands L.

The invention accordingly also relates in particular to transition metal complexes in which the tridentate, dianionic, halogen-free ligands (O~N~O)$^{2-}$ occupy three meridional coordination sites around the cobalt.

In the oxidative carbonylation of an amine under halogen-free reaction conditions to give the corresponding ureas, the catalysts described above afford conversions and selectivities of up to 99%, i.e. yields of up to 99%, based on the amine used, according to the following general equation:

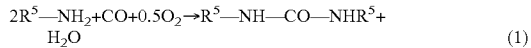

$$2R^5{-}NH_2 + CO + 0.5 O_2 \rightarrow R^5{-}NH{-}CO{-}NHR^5 + H_2O \qquad (1)$$

$R^5$ is a primary or secondary aliphatic radical or an aromatic radical. It is also possible to use mixtures of different amines $R^5{-}NH_2$, in which case the urea formed is asymmetrically substituted. $R^5{-}NH_2$ here is not only a monofunctional amine but also one amino group equivalent of a di- or polyamine compound (e.g. $R^5{=}CH_3{-}C_6H_3{-}NH_2$, i.e. $R^5{-}NH_2$=toluoylenediamine). In di- or polyamine compounds all the primary amino groups preferably react according to equation (1). Within the framework of the present invention, aliphatic radicals are understood as meaning linear, branched and also cyclic aliphatic radicals.

Preferably, the process according to the invention is carried out in the presence of organic compounds carrying hydroxyl groups. This embodiment of the invention accordingly relates to a process wherein the oxidative carbonylation of organic amines is carried out in the presence of organic compounds carrying hydroxyl groups and leads to the preparation of urethanes or mixtures of urethanes and ureas. The urethanes are formed according to the following general equation:

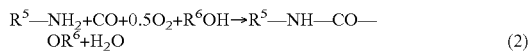

$$R^5{-}NH_2 + CO + 0.5 O_2 + R^6OH \rightarrow R^5{-}NH{-}CO{-}OR^6 + H_2O \qquad (2)$$

$R^6$ is a primary or secondary aliphatic radical or an aromatic radical. $R^5$ and $R^6$ can also be identical. $R^6OH$ here is not only a monofunctional hydroxyl compound but also one hydroxyl group equivalent of a di- or polyhydroxyl compound.

The reactions according to equations (1) and (2) can also proceed in parallel with one another and lead to mixtures of urethanes and ureas.

Suitable organic amines for the process according to the invention for the preparation of urethanes and/or ureas are primary and secondary amines, primary amines (i.e. organic amines containing primary amine groups "—NH$_2$") being preferred because the urethanes and/or ureas obtained therefrom can be converted to the corresponding isocyanates in a subsequent process step, e.g. by thermolysis with cleavage of the hydroxyl compound $R^6OH$ or the amine compound $R^5NH_2$. Suitable primary amines are particularly aliphatic mono-, di- and/or polyamines, mixed aliphatic/cycloaliphatic mono-, di- and/or polyamines, cycloaliphatic mono-, di- and/or polyamines, aromatic mono-, di- and/or polyamines, araliphatic mono-, di- and/or polyamines or mixtures containing two or more of the above primary amines. Thus the invention further relates to a process for the oxidative carbonylation of organic amines wherein the organic amines used are aliphatic, cycloaliphatic, araliphatic and/or aromatic mono- or diamines.

Preferred examples of suitable primary monoamines are aniline, anilines mono- or polysubstituted on the aromatic ring, such as the isomeric toluidines or halogenated anilines, benzylamine, 2-phenylethylamine, 1-phenylethylamine, cyclohexylamine, substituted cyclohexylamines, methylamine, ethylamine, the isomeric propyl-, butyl- and pentylamines and their higher homologues.

Preferred examples of suitable primary diamines are o-phenylenediamine, m-phenylenediamine, p-phenylenediamine, phenylenediamines mono- or polysubstituted on the aromatic ring, such as tetramethylphenylenediamine, the isomeric diaminotoluenes, such as 2,4-diaminotoluene and 2,6-diaminotoluene, the isomeric diaminodiphenylmethanes, such as 4,4'-diaminodiphenylmethane, 2,4'-diaminodiphenylmethane or 2,2'-diaminodiphenylmethane, naphthalenediamines, such as 1,4-naphthalenediamine, 1,5-naphthalenediamine or 1,8-naphthalenediamine, o-xylylenediamine, m-xylylenediamine, p-xylylenediamine, the isomeric diaminocyclohexanes, diaminocyclohexanes substituted on the cycloaliphatic ring, isophoronediamine, ethylenediamine, 1,2-diaminopropane, α,ω-diaminoalkanes, such as 1,3-diaminopropane and higher homologues, e.g. 1,6-hexamethylene-diamine, and substituted α,ω-diaminoalkanes.

The invention especially provides a process for the oxidative carbonylation of organic amines wherein the aromatic amines used are aniline or toluylenediamine, preferably aniline.

Preferred examples of suitable primary polyamines are mixtures of the isomeric diaminodiphenylmethanes with their higher homologues and their isomers of the polyfunctional amines of the diphenylmethane series, obtained by condensing aniline with formaldehyde.

Preferred examples of organic compounds containing one or more hydroxyl groups are alcohols, especially aliphatic alcohols, such as methanol, ethanol and the higher homologous alkanols and their isomers, such as n-propanol, isopropanol, n-butanol, isobutanol, sec-butanol, etc., derivatives of the aforementioned alcohols mono- or polysubstituted by halogen, such as trifluoroethanol or hexafluoroisopropanol, cycloaliphatic alcohols, such as cyclopentanol or cyclohexanol, benzyl alcohol, phenol or substituted phenols (e.g. cresols). Particularly preferably, the invention relates to a process wherein the organic compounds carrying hydroxyl groups are selected from the group comprising:
methanol, ethanol, n-butanol, isobutanol, sec-butanol, n-propanol and isopropanol.

The invention further relates to a process wherein the transition metal complex catalyst containing the structural feature $[M^{n+}(O{\sim}N{\sim}O)^{2-}]^{(n-2)+}(L)_m(Z^-)_{n-2}$ is present in a concentration of 0.01 mol % to 10 mol %, preferably of 0.05 mol % to 5.0 mol % and particularly preferably of 0.1 mol % to 3.0 mol %, based on one mol of primary amino groups.

In the oxidative carbonylation of an amine in the presence of a compound containing hydroxyl groups to give the corresponding urethanes, the compound containing hydroxyl groups is used in at least the stoichiometric quantity, based on the quantity of amino groups. It is preferable to use an excess of the compound containing hydroxyl groups, based on the quantity of amino groups. The quantity of hydroxyl groups used per mol of primary amino groups is particularly preferably 2 mol-100 mol, very particularly preferably 5 mol-50 mol.

In general, the compound containing hydroxyl groups serves as a solvent, especially when it is used in excess.

However, it is also possible to use another solvent. Possible additional solvents are any solvents that are inert under the reaction conditions. Preferred examples of suitable solvents are aliphatic and aromatic hydrocarbons and their halogenated derivatives, e.g. benzene, toluene, the isomeric xylenes, ethylbenzene, chlorobenzene, the isomeric dichlorobenzenes, ethers, esters, etc. Particularly preferred solvents are benzene, toluene, the isomeric xylenes, ethylbenzene, halogen-free ethers and halogen-free esters.

In another embodiment, it is also possible to use solvents containing water.

The reaction is preferably carried out in the temperature range from 20° C. to 260° C., particularly preferably at 80° C. to 220° C.

The quantity of carbon monoxide is proportioned so that it is present in at least the stoichiometric quantity required for the reaction, based on the amino groups present. It is preferable to use at least 10 times, particularly at least 15 times, the stoichiometrically required quantity of carbon monoxide. In general, at most 200 times the stoichiometrically required quantity of carbon monoxide is used. The absolute partial pressure of the carbon monoxide used is preferably 1.0 bar to 150 bar, particularly preferably 10 bar to 100 bar, at room temperature.

The quantity of oxygen is proportioned so that it is present in at least the stoichiometric quantity required for the reaction, based on the amino groups present. It is preferable to use at least 1.2 times, particularly at least 1.6 times, the stoichiometrically required quantity of oxygen. In general, at most 20 times the stoichiometrically required quantity of oxygen is used. The absolute partial pressure of the oxygen used is preferably 0.1 bar to 20 bar, particularly preferably 1.0 bar to 10 bar, at room temperature. However, the process is always operated outside the explosive limits of the $CO/O_2$ system.

Thus the invention further relates to a process wherein the oxidative carbonylation is carried out at temperatures of 20° C. to 260° C., at an absolute carbon monoxide partial pressure of 1.0 bar to 150 bar and at an absolute oxygen partial pressure of 0.10 bar to 20 bar.

The oxygen can be provided either as pure oxygen or as a mixture with gases that are inert under the reaction conditions, e.g. nitrogen, $CO_2$, noble gases, etc., it being possible to use either one of these inert gases or a mixture of two or more of said inert gases. It is preferable to use either pure oxygen or air.

In the process according to the invention, the oxidative carbonylation of an amine in the presence of a compound containing hydroxyl groups leads to the formation of the corresponding urethanes. The ureas based on the amine may also optionally appear as intermediates and/or by-products during the reaction; these ureas can further react partially or completely in the subsequent course of the reaction, by alcoholysis with the compound containing hydroxyl groups, to give the corresponding urethanes.

In principle, however, the ureas can also be specifically prepared by the oxidative carbonylation of organic amines with carbon monoxide and oxygen in the absence of organic compounds carrying hydroxyl groups.

The reaction mixture can be worked up and the product isolated by the methods known to those skilled in the art or any combinations of the known methods, e.g. distillation, crystallization, filtration, extraction, membrane separation methods, etc. Educts, intermediates, solvents and/or catalysts can be recovered and recycled into the process at the appropriate point.

The process can be carried out batchwise, semi-continuously or continuously.

Preferably, the urethane obtained can be converted to the corresponding isocyanate, e.g. thermally or chemically, in a further stage of the process. Thermolysis can take place e.g. with or without a catalyst, in bulk or in the presence of a suitable solvent. The compound containing hydroxyl groups can be recovered and re-used in the urethane synthesis. The process as a whole can be made economically more attractive by closing the circuit of the compound containing hydroxyl groups, since it is then only necessary to compensate losses of said compound that are due to irreversible secondary reactions. The ureas can also be subjected to cleavage into the isocyanate in this way, albeit under more rigorous conditions. However, it is preferable to use the urethanes.

Thus the invention also relates to a process for the preparation of isocyanates by the thermal cleavage of urethanes or ureas, wherein urethanes or ureas are prepared by oxidative carbonylation of the appropriate amines by the process according to the invention using the transition metal complexes according to the invention, and are then thermally converted to the corresponding isocyanates.

The carbonylation and the thermolysis are preferably carried out in one process step.

The process according to the invention is illustrated in greater detail by means of the Examples which follow.

EXAMPLES

Example 1

According to the Invention 0.0592 g (0.22 mmol) of salicylidene-aminophenol-cobalt (II) ([$Co^{II}$(Sap)], cf. also scheme (vi)), 1.023 g (11.0 mmol) of aniline and 10.692 g (297.2 mmol) of methanol were mixed in a 100 $cm^3$ stainless steel autoclave with a polytetrafluoroethylene beaker as insert. The autoclave was filled at room temperature (ca. 25° C.) with a mixture of oxygen gas (4 bar) and carbon monoxide gas (36 bar). When the introduction of gas into the autoclave had been stopped, the latter was placed in an aluminium heating block heated to 200° C. Within 5 minutes the autoclave reached a reaction temperature of 165° C., which was then kept constant. After a reaction time of 3 hours, the autoclave was cooled with cold water and ice for about 5 minutes until it reached room temperature. The reaction mixture was then examined qualitatively and quantitatively by gas chromatography using naphthalene as internal standard. The aniline conversion was 100% and the yield of methyl N-phenylcarbamate was 99%.

Example 2

According to the Invention

The reaction given in Example 1 was repeated with 0.22 mmol of azobisphenol-cobalt(II) ([$Co^{II}$(Abp)], cf. also scheme (vi)) as catalyst under otherwise identical conditions.

Example 3

According to the Invention

The reaction given in Example 1 was repeated with 0.22 mmol of naphthalideneaminophenol-cobalt(II) ([$Co^{II}$(Nap)], cf. also scheme (vi)) as catalyst under otherwise identical conditions.

Example 4

According to the Invention

The reaction given in Example 1 was repeated with 0.22 mmol of salicylideneaminonaphthalenol-cobalt(II) ([Co$^{II}$(San)], cf. also scheme (vi)) as catalyst under otherwise identical conditions.

Example 5

According to the Invention

The reaction given in Example 1 was repeated with 0.22 mmol of hydroxyphenylquinolinol-cobalt(II) ([Co$^{II}$(Pqo)], cf. also scheme (vi)) as catalyst under otherwise identical conditions.

Scheme (vi): catalysts according to the invention of Examples 1 to 5

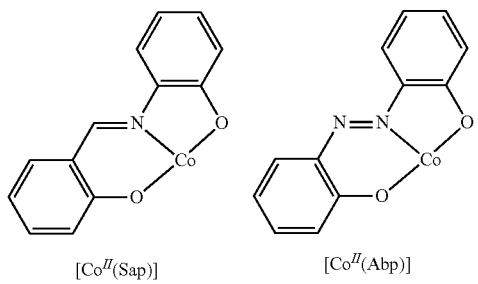

[Co$^{II}$(Sap)]    [Co$^{II}$(Abp)]

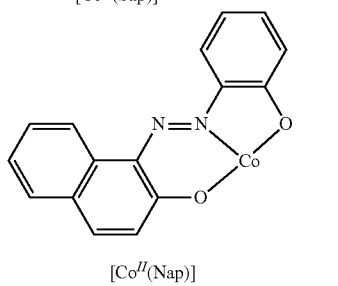

[Co$^{II}$(Nap)]

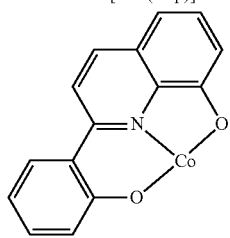

[Co$^{II}$(Pqo)]

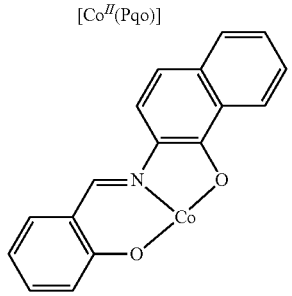

[Co$^{II}$(San)]

Example 6

Comparative Example

The reaction given in Example 1 was repeated without catalyst under otherwise identical conditions.

Example 7

Comparative Example

The reaction given in Example 1 was repeated with 0.22 mmol of cobalt(II) acetate tetrahydrate, Co$^{II}$(OAc)$_2$, as catalyst under otherwise identical conditions.

The results are collated in the Table below:

TABLE 1[a]

Results of Examples 1 to 7

| Example No. | Catalyst[b] | Conversion[c] [%] | Selectivity[d] [%] | Yield[d] [%] |
|---|---|---|---|---|
| 1 | [Co$^{II}$(Sap)] | 100 | 99 | 99 |
| 2 | [Co$^{II}$(Abp)] | 100 | 93 | 93 |
| 3 | [Co$^{II}$(Nap)] | 99 | 91 | 90 |
| 4 | [Co$^{II}$(San)] | 93 | 80 | 74 |
| 5 | [Co$^{II}$(Pqo)] | 88 | 87 | 77 |
| 6 (Comparison) | — | 12 | not determined | not determined |
| 7 (Comparison) | Co$^{II}$(OAc)$_2$ | 66 | 45 | 30 |

[a]reaction conditions: 165° C., 4 bar O$_2$, 36 bar CO, reaction time = 3 h, molar ratio of catalyst to aniline = 1/50, molar ratio of methanol to aniline = 27/1
[b]Abp = azobisphenol, Nap = naphthalideneaminophenol, Pqo = hydroxyphenyl-quinolinol, Sap = salicylideneaminophenol, San = salicylideneamino-naphthalenol, OAc = acetate
[c]of aniline
[d]based on methyl N-phenylcarbamate

Example 8

According to the Invention

The catalyst of Example 2 was used in a molar ratio of catalyst to aniline of 1/200 under otherwise identical conditions.

Example 9

Comparative Example

Example 8 was repeated with the addition of NaI in a molar ratio of NaI to aniline of 1/10.

The results are compared in Table 2:

TABLE 2[a]

Results of Examples 8 and 9

| Example No. | Catalyst[b] | Conversion[c] [%] | Selectivity[d] [%] | Yield[d] [%] |
|---|---|---|---|---|
| 8 | [Co$^{II}$(Abp)] | 65 | 69 | 45 |
| 9[e] (Comparison) | [Co$^{II}$(Abp)] | 63 | 67 | 42 |

[a]reaction conditions: 165° C., 4 bar O$_2$, 36 bar CO, reaction time = 3 h, molar ratio of catalyst to aniline = 1/200, molar ratio of methanol to aniline = 27/1
[b]Abp = azobisphenol
[c]of aniline
[d]based on methyl N-phenylcarbamate
[e]carried out with the addition of 10 mol % of NaI (based on aniline)

As can be seen in Table 2, a reduction in catalyst loading leads to a reduction in yield and selectivity (cf. Example 8 with Example 2). However, the catalysts according to the invention are so efficient that they render the use of halogen-containing promoters superfluous even under such difficult conditions (cf. Example 8 with Example 9).

The invention claimed is:

1. A process for the preparation of urethane or urea or mixtures of urethane and urea by the oxidative carbonylation of organic amines containing primary amino groups in the presence of carbon monoxide, oxygen and a catalyst, comprising utilizing as the catalyst a transition metal complex containing the structural feature $[M^{n+}(O\sim N\sim O)^{2-}]^{(n-2)+}(L)_m(Z^-)_{n-2}$, wherein:

M is a transition metal selected from the group consisting of Co, Ni, Cu, Rh, Ru, Ir and Pt, n is 2 or 3, $(O\sim N\sim O)^{2-}$ is a tridentate, dianionic chelating ligand coordinating with M via two oxygen atoms and one nitrogen atom, which is derived by deprotonation of all the OH groups of a neutral chelating ligand selected from the group consisting of:

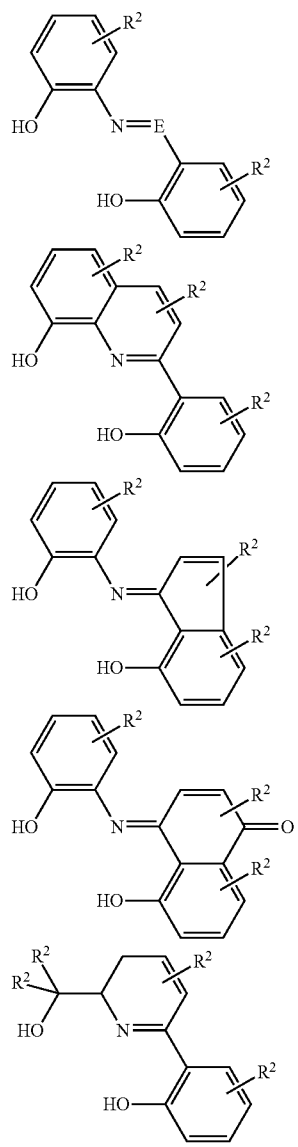

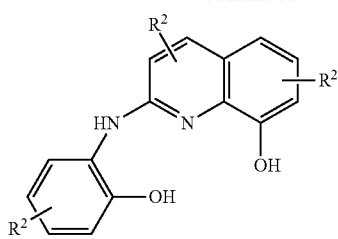

I

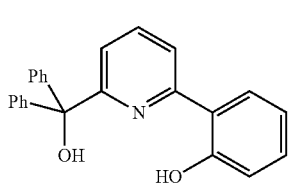

II

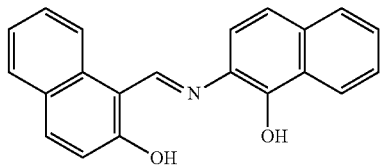

III

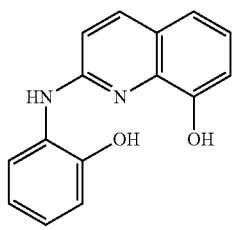

IV

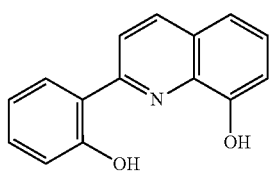

V

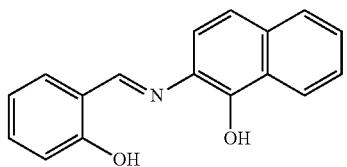

VI

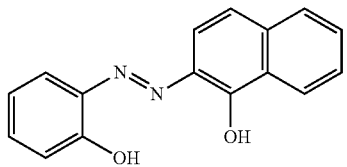

VII

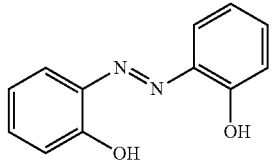

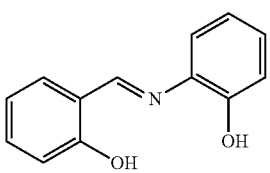

VII and combinations thereof,

L is a neutral ligand selected from the group consisting of water, azaaromatics, cyclic amines, acyclic amines, cyclic carboxamides, acyclic carboxamides, cyclic carboxylic acid esters, acyclic carboxylic acid esters, cyclic ketones, acyclic ketones, cyclic ketimines, acyclic ketimines, aliphatic ethers, aliphatic alcohols, aromatic alcohols, sulfoxides, formamides, cyclic organocarbonates, acyclic organocarbonates and nitriles, m is 0, 1, 2 or 3 and $Z^-$ is a monoanionic ligand selected from the group consisting of sulfonates, carboxylates, pseudohalides, $[BF_4]^-$, $[PF_6]^-$, $[SbF_6]^-$, nitrate, hydrogensulfate, fluorosulfate and methylsulfate, and carrying out the process under halogen-free reaction conditions.

2. The process according to claim 1 wherein $Z^-$ is tosylate, mesylate, acetate, benzoate, cyanide, cyanate, thiocyanate, azide, nitrate, hydrogensulfate or methylsulfate.

3. The process according to claim 1 wherein the transition metal M is cobalt.

4. The process according to claim 1 wherein the catalyst is present in a concentration of 0.01 mol % to 10 mol %, based on one mol of primary amino groups.

5. The process according to claim 1 wherein the oxidative carbonylation is carried out at temperatures of 20° C. to 260° C., at an absolute carbon monoxide partial pressure of 1.0 bar to 150 bar and at an absolute oxygen partial pressure of 0.10 bar to 20 bar.

6. The process according to claim 1 wherein the oxidative carbonylation of organic amines is carried out in the presence of organic compounds carrying hydroxyl groups and leads to the preparation of urethanes or mixtures of urethanes and ureas.

7. The process according to claim 6 wherein the organic compounds carrying hydroxyl groups are:
methanol, ethanol, n-butanol, isobutanol, sec-butanol, n-propanol or isopropanol.

8. The process according to claim 1 wherein the organic amines are aliphatic, cycloaliphatic, araliphatic and/or aromatic mono- or diamines.

9. Process according to claim 8 wherein the aromatic amines are aniline or toluylenediamine.

* * * * *